(12) United States Patent
Engelhardt

(10) Patent No.: US 9,804,375 B2
(45) Date of Patent: Oct. 31, 2017

(54) 4PI STED FLUORESCENCE LIGHT MICROSCOPE WITH HIGH THREE-DIMENSIONAL SPATIAL RESOLUTION

(71) Applicant: Deutsches Krebsforschungszentrum, Heidelberg (DE)

(72) Inventor: Johann Engelhardt, Bad Schoenborn (DE)

(73) Assignee: DEUTSCHES KREBSFORSCHUNGSZENTRUM, Heidelberg (DE)

(*) Notice: Subject to any disclaimer, the term of this patent is extended or adjusted under 35 U.S.C. 154(b) by 377 days.

(21) Appl. No.: 14/497,675

(22) Filed: Sep. 26, 2014

(65) Prior Publication Data
US 2015/0009558 A1 Jan. 8, 2015

Related U.S. Application Data

(63) Continuation of application No. PCT/EP2013/058461, filed on Apr. 24, 2013.

(30) Foreign Application Priority Data

Apr. 24, 2012 (EP) .................................... 12165276

(51) Int. Cl.
G02B 21/00 (2006.01)
G01N 21/64 (2006.01)

(52) U.S. Cl.
CPC ..... G02B 21/0076 (2013.01); G01N 21/6458 (2013.01); G02B 21/0032 (2013.01)

(58) Field of Classification Search
CPC ............ G02B 21/0076; G02B 21/0032; G02B 21/16; G01N 21/6458

(Continued)

(56) References Cited

U.S. PATENT DOCUMENTS 7,724,351 B2 * 5/2010 Loopstra ............. G03F 7/70308
355/63
2002/0030886 A1 * 3/2002 Bewersdorf ........... G02B 21/06
359/387

(Continued)

FOREIGN PATENT DOCUMENTS

DE 10 2008 019 957 A1 11/2009
WO 2011/086519 A1 7/2011

OTHER PUBLICATIONS

Serway et al. "College Physics" 1985, Saunders College Publishing, p. 619 equation 26.3.*

(Continued)

*Primary Examiner* — Ricky Mack
*Assistant Examiner* — Kristina Deherrera
(74) *Attorney, Agent, or Firm* — Thomas | Horstemeyer, LLP

(57) ABSTRACT

An apparatus forming an area of minimum light intensity enclosed by high light intensity includes two objectives focusing light of opposite directions into a common focal area. Light intensities of a first pair of light beams extinguish each other in a first partial area of the focal area. Beam paths of the first pair of beams pass through the objectives in a first pair of partial areas of the pupils of the objectives. Light intensities of a second pair of light beams extinguish each other in a second partial area of the focal area. Beam paths of the second pair of light beams pass through the objectives in a second pair of partial areas which are offset with regard to the first pair of partial areas of the pupils; and the light of the second pair does not interfere with the light of the first pair of light beams.

14 Claims, 6 Drawing Sheets

(58) Field of Classification Search
USPC .................................................. 359/385–389
See application file for complete search history.

(56) References Cited

U.S. PATENT DOCUMENTS

2006/0109547 A1\* 5/2006 Engelhardt .......... G02B 21/241
359/385
2011/0273768 A1\* 11/2011 Krishnamachari
.......................... G02B 21/0032
359/388

OTHER PUBLICATIONS

Fischer Joachim, Wegener Martin: "Three-dimensional optical laser . . . ", Laser Photonics Rev., 1-23, (2012)/DOI 10.1002/lpor.201100046.
Dyba M et al: "Phase filter enhanced STED-4Pi . . . ", New Journal of Physics, Institute of Physics Publishing, Bristol, GB, vol. 7, (2005), 134, pp. 1-21.
Hongki Yoo et al: "Effects of a pupil filter on stimulated . . . ", Three-Dimensional and Multi-Dimensional Microscopy: Image Acquisition and Processing XIII, Bellingham, USA, vol. 6090, (2006), pp. 60900X-1-60900X-6.
Haeberlé O et al: "Improving the lateral resolution . . . ", Optics Communications, North-Holland Publishing Co., Amsterdam, NL, vol. 259, (2006), pp. 400-408.
International Search Report in co-pending, related PCT application PCT/EP2013/058461, dated Jun. 28, 2013.

\* cited by examiner

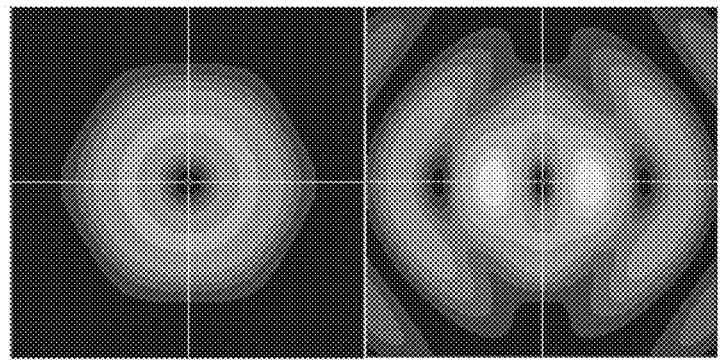
(c)
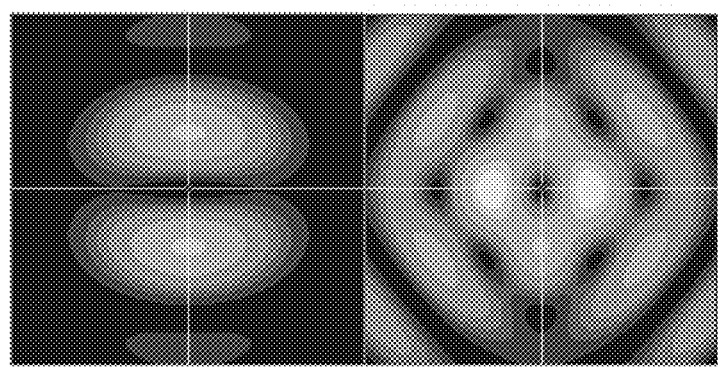
(b)
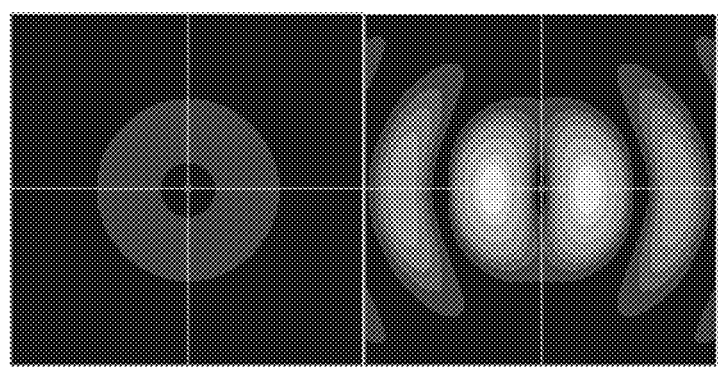
(a)
Fig. 5

4PI STED FLUORESCENCE LIGHT MICROSCOPE WITH HIGH THREE-DIMENSIONAL SPATIAL RESOLUTION

CROSS REFERENCE TO RELATED APPLICATIONS

This application is a continuation of International Application PCT/EP2013/058461 with an International Filing Date of Apr. 24, 2013 and claiming priority to European Patent Application No. 12 165 276.2 entitled "4Pi STED Fluorescence Light Microscope With High Three-Dimensional Spatial Resolution", filed on Apr. 24, 2012.

FIELD OF THE INVENTION

The present invention generally relates to an apparatus for forming a three-dimensional light intensity distribution comprising a spatially limited area of minimum light intensity that is enclosed by areas of higher light intensity.

Such an apparatus is, for example, used in so-called STED, GSD and RESOLFT scanning fluorescence light microscopy to achieve a spatial resolution beyond the diffraction barrier in imaging a structure in a sample marked with a fluorescent marker. In these applications the three-dimensional light intensity distribution comprising the spatially limited area of minimum light intensity is formed of fluorescence inhibiting light, i.e. of an optical signal to the fluorescent marker which inhibits or stops the fluorescent marker from spontaneously emitting fluorescence light. If the minimum light intensity in the spatially limited area is low, i.e. zero or close to zero, and if the higher light intensities in the areas enclosing the spatially limited area of minimum light intensity completely inhibit the spontaneous emission of fluorescence light, the area in which the fluorescent marker is still capable of emitting fluorescence light can be reduced beyond the diffraction barrier.

There are, however, other applications of apparatus forming a three-dimensional light intensity distribution comprising a spatially limited area of minimum light intensity that is enclosed by areas of higher light intensity, like for example in optical traps or optical lithography, see, for example, Joachim Fischer, Martin Wegener: Three-dimensional optical laser lithography beyond the diffraction limit, Laser Photonics Rev., 1-23 (2012)/DOI 10.1002/lpor.201100046.

BACKGROUND OF THE INVENTION

In STED, GSD and RESOLFT scanning fluorescence light microscopy it is known to form a three-dimensional light intensity distribution comprising a spatially limited area of minimum light intensity that is enclosed by areas of higher light intensity of fluorescence inhibiting light by means of shaping the wave fronts of a beam of coherent fluorescence inhibiting light by means of a phase plate. One known phase plate for this application is a so-called phase clock which provides a phase shift increasing from zero to $2\pi$ over one turn about the optical axis, corresponding to an optical path difference of $\lambda$ which is the wavelength of the fluorescence inhibiting light. When the beam of the fluorescence inhibiting light, after passing this phase clock and after the fluorescence inhibiting light being circularly polarized, is focused into a focal area by means of an objective, the resulting light intensity distribution comprises a zero point in the focal area enclosed by a torus of higher light intensity around the optical axis, which is often called a doughnut. By means of this light intensity distribution of fluorescence inhibiting light the spatial resolution of scanning fluorescence light microscopy will be enhanced within the focal plane of the objective, i.e. in x- and y-directions, but not normal to the focal plane, i.e. in z-direction.

In so-called 4Pi STED scanning fluorescence light microscopy, it is known to use an apparatus for forming a three-dimensional light intensity distribution comprising a spatially limited area of minimum light intensity that is enclosed by areas of higher light intensity of the fluorescence inhibiting light, which comprises two objectives facing each other on a common optical axis. These objectives focus light coming out of opposite directions into a common focal area. Fluorescence inhibiting light from a coherent light source is split into a pair of coherent light beams and each of the two objectives focuses one of these coherent light beams into the common focal area. If the beam paths of the two coherent light beams which each extend from the beam splitters through one of the objectives and to the common focal area differ in optical length by $\lambda(2n+1)/2$, the light intensities of the coherent light beams extinguish each other in a partial area of the focal area extending along the focal planes of the objectives. This area of minimum light intensity is enclosed by areas of higher light intensity of the fluorescence inhibiting light on both sides in direction of the common optical axis. Thus, in 4Pi STED fluorescence light microscopy the spatial resolution is enhanced in the z-direction of the common optical axis but neither in x- nor in y-direction. This spatial resolution in x- and y-direction may be enhanced by means of a confocal detection arrangement of the fluorescence light registered from the respective sample.

Dyba M et al "Phase filter enhanced STED-4Pi fluorescence microscopy: theory and experiment", NEW JOURNAL OF PHYSICS, INSTITUTE OF PHYSICS PUBLISHING, BRISTOL, GB, besides standard 4Pi STED scanning fluorescence light microscopy, report a study of phase modifications of the wavefront of the stimulating beam that strengthen weakly transferred frequencies within the optical transfer-function of a 4Pi STED microscope. The enlarged bandwidth shall enable the separation of objects at 76 nm axial distance.

Hongki Yoo, Incheon Song, Taehoon Kim, Daegab Gweon "Effects of a pupil filter on stimulated emission depletion microscopy", THREE-DIMENSIONAL AND MULTIDIMENSIONAL MICROSCOPY, IMAGE ACQUISITION AND PROCESSING XIII, BELLINGHAM, USA, report effects of a pupil filter on the performances of STED-scanning fluorescence light microscopy. Using a half-coated phase plate, a zero-centered spot is made with a narrow and steep gap at the center to achieve a high lateral resolution. Numerical and experimental results show that by simply inserting a central obstacle as a pupil filter, it is possible to reduce the central gap of the zero-centered spot. However, in order to compensate inevitable loss of light, which is blocked by the obstacle, increased laser power is required.

Haeberle O et al "Improving the lateral resolution in confocal fluorescence microscopy using laterally interfering excitation beams", OPTICS COMMUNICATIONS, NORTH-HOLLAND PUBLISHING CO., AMSTERDAM, NL, disclose an STED-scanning fluorescence light microscopy variant in which the lateral resolution is based on laterally interfering beams. A half phase plate is used to modify the illumination, combined with a laterally offset detection. Another approach uses several excitation beams, slightly shifted and properly dephased, to decrease the lateral extension of the point spread function (PSF).

WO 2011/086519 A1 discloses an STED microscopy system in which an optical element is supplied for focusing a first excitation and a second depletion beam on an object, thereby defining a common optical path for both the first and the second beam. A phase modifying member is inserted in the common optical path, and the phase modifying member is optically configured for leaving the wavefront of the first beam substantially unchanged, and for changing the wavefront of the second beam so as to create an undepleted region of interest in the object.

In so-called isoSTED scanning fluorescence light microscopy which is, for example, described in DE 10 2008 019 957 A1, an apparatus including a phase plate and an apparatus including two objectives facing each other are combined for forming a three-dimensional light intensity distribution of fluorescence inhibiting light enhancing the spatial resolution by means of the fluorescence inhibiting light both in x- and y- and in z-directions. In this combined apparatus, it has to be cared for that the light of the beam of coherent light passing through the phase plate and then being focused into the focal area does not interfere with the light of the pair of coherent light beams focused and superimposed by the two objectives. If this care is not taken, the light intensities of the two individual three-dimensional light intensity distributions will not simply add up but may interfere with each other, i.e. mutually affect each other.

An apparatus which would allow for generating a three-dimensional light intensity distribution comprising an even steeper light intensity gradient between the area of minimum light intensity to the enclosing areas of higher light intensity than in isoSTED considering same light intensities would be desirable.

SUMMARY OF THE INVENTION

The invention relates to an apparatus for forming a three-dimensional light intensity distribution comprising a spatially limited area of minimum light intensity that is enclosed by areas of higher light intensity. The apparatus according to the present invention comprises two objectives which are facing each other on a common optical axis, which focus light coming out of opposite directions into a common focal area, and which each have a pupil, and at least one light source. The apparatus according to the present invention further comprises a first pair of beam paths each extending from the at least one light source, through one of the objectives and to the common focal area, wherein light intensities of a first pair of coherent light beams each coming from the at least one light source and running along one of the beam paths of the first pair of beam paths extinguish each other in a first partial area of the focal area by destructive interference. In the apparatus according to the present invention, these beam paths of the first pair of beam paths pass through the two objectives in a first pair of partial areas of the pupils of the objectives centered on opposite sides of the common optical axis. The apparatus of the present invention further comprises a second pair of beam paths each extending from the at least one or a second light source, through one of the objectives and to the common focal area, wherein light intensities of a second pair of coherent light beams each coming from the at least one or a second light source and running along one of the beam paths of the second pair of beam paths extinguish each other in a second partial area of the focal area by destructive interference and wherein the beam paths of the second pair of beam paths pass through the two objectives in a second pair of partial areas of the pupils of the objectives centered on opposite sides of the common optical axis. The partial areas of the pupils of the second pair of partial areas of the pupils of the objectives are offset in rotation direction about the common optical axis with regard to the partial areas of the pupils of the first pair of partial areas of the pupils of the objectives, and the light of the second pair of coherent light beams do not interfere with the light of the first pair of coherent light beams.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

FIG. 5 shows the total light intensity distributions resulting from the interference between two coherent light beams each covering the full pupil of the two objectives facing each other, resulting from a superposition of the two light intensity distributions according to FIG. 4, and resulting from a superposition of three such light intensity distributions arranged in a rotational symmetric arrangement with respect to the optical axis, each total light intensity distribution being displayed in discrete gray levels, and both in a section along the common focal plane of the objectives (top) and in a section orthogonal to the common focal plane of the objectives (bottom).

DETAILED DESCRIPTION

Figure 1:
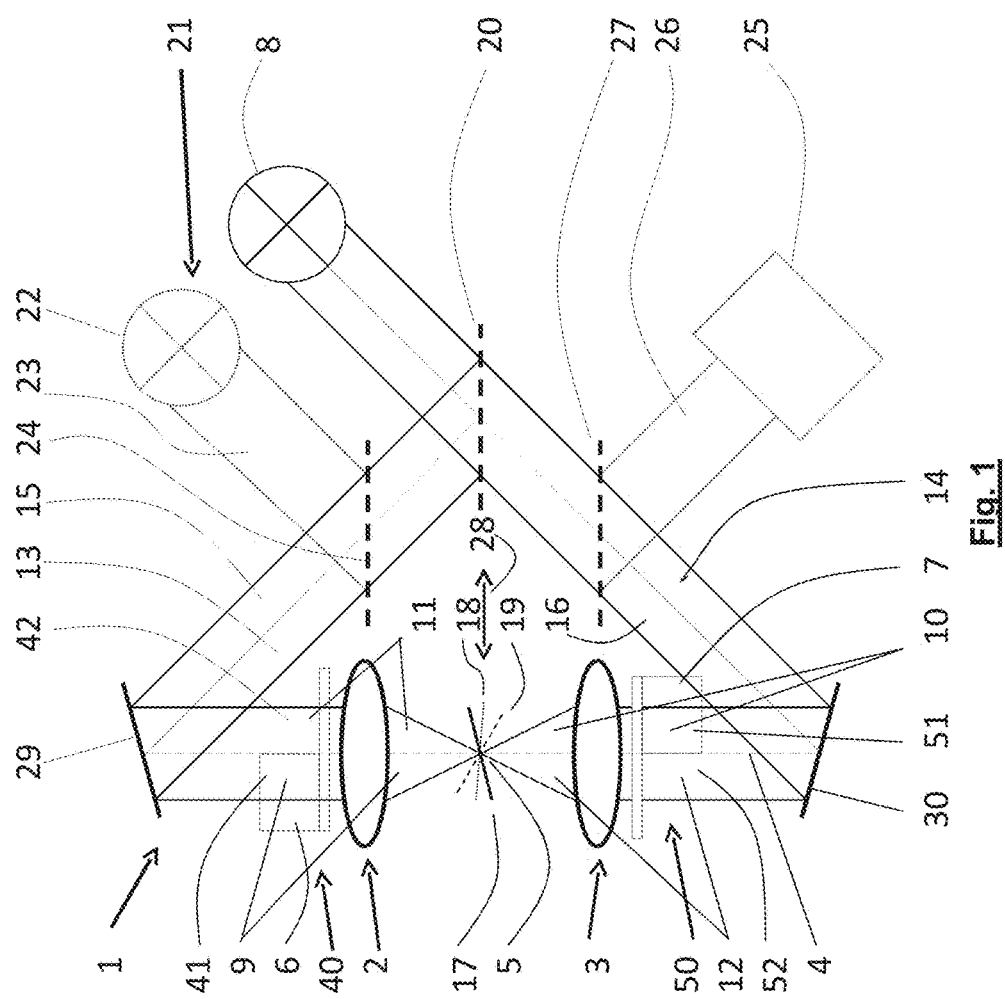
FIG. 1 is a schematic drawing showing a first embodiment of the apparatus according to the present invention.

In the apparatus according to the present invention, the partial areas of the pupils of each pair of partial areas of the pupils centered on opposite sides of the common optical axis have the effect that the partial area of the focal area in which the light intensities extinguish each other by destructive interference, i.e. the spatially limited area of minimum light intensity, normally extending along the focal planes of the two objectives is tilted with regard to the common focal plane in the direction in which the partial areas of the pupil are offset from the common optical axis. With two pairs of coherent light beams which pass through the pupils of the objective in different pairs of partial areas of the pupils about the optical axis, and which do not interfere with each other but whose light intensity distributions simply add up in the focal area, the overall three-dimensional light intensity distribution in the focal area shows a spatially limited area of minimum light intensity which is reduced to a small volume extending along an axis running through the focal area along the focal planes of the objectives. In case of three or more pairs of coherent light beams, the area of minimum light intensity is reduced to a small volume within the focal area, the volume being spatially limited in all directions.

An interference between the different pairs of coherent light beams may be avoided in various ways. Basically, at least one of (i) a coherence, (ii) an identity of the wavelengths, (iii) an identity of the polarizations and (iv) a coincidence in time of the different pairs of coherent light beams may be avoided to avoid their optical interference, More detailed examples will be given below.

The coherence of the different pairs of coherent light beams may be avoided in that the different pairs of coherent light beams are provided by different light sources, or in that the optical path lengths of the different pairs of coherent light beams differ by more than a coherence length of the at least one light source providing both or all different pairs of coherent light beams.

The coherence length of the at least one and any other light source will depend on the particular type of light source used. Preferably, the coherence length is long enough to easily provide the pairs of coherent light beams, i. e. to provide for a coherence of the light beams within each of theses pairs. If the at least one light source provides both or all different pairs of coherent light beams and if the coherence of the different pairs of coherent light beams is to be avoided by different optical path lengths, however, the coherence length of the at least one light source should not be too long, as this would require corresponding long differences in optical path length. The at least one and any other light source used may, for example, be a laser or a laser diode, such as a laser diode normally used in a DVD drive.

The formulation "partial areas of the pupils of the objectives centered on opposite sides of the common optical axis" means that the centers of these partial areas of the pupil are offset from the common optical axis in opposite directions. In the present context, the geometrical centers of the partial areas of the pupils are of less importance than the centers of intensity of the coherent light beams of the pair of coherent light beams passing through this pair of partial areas of the pupils of the objectives. With a uniform intensity distribution over the partial areas of the pupils of the objectives, however, there will be no difference.

Generally, the partial areas of the pupils of the pairs of the pupils of the objectives may include or extend beyond the common optical axis. However, it is preferred that the partial areas of the pupils of the pairs of the partial areas of the pupils of the objectives do not extend beyond the common optical axis to have a more pronounced tilt of the resulting planes of minimum light intensity of each pair of coherent light beams.

As the light intensities of the different pairs of coherent light beams may anyway not interfere with each other, the partial areas of the pupil of each of the objectives through which the different beam paths pass towards a common focus may generally overlap. However, it is preferred that they do not overlap. This allows to separately treat or modify the different beam paths with different optical elements.

Preferably, the two partial areas of each pair of partial areas of the pupils of the objectives are point symmetric with regard to the focal area. This facilitates generating a zero point, or a light intensity close to zero, of the overall light intensity distribution at a centre of the focal area.

Further, the partial areas of the pupil of each of the objectives through which the different beam paths pass towards the common focal area are preferably rotation symmetric with regard to the common optical axis. This symmetry facilitates having symmetric areas of high light intensity enclosing the area of minimum light intensity and in forming a spherical area of minimum light intensity within the focal area.

To have a zero point of the light intensity distribution in a partial area of the focal area as a result of the interference of the two coherent light beams of each pair of coherent light beams, the two beam paths of each pair of beam paths should differ from each other in optical length by $\lambda(2n+1)/2$, wherein $\lambda$ is the wavelength of the light of the coherent light beams running along these beam paths, and n is an integer.

The two beam paths of the first pair of beam paths may part from each other in a first beam splitter which splits light coming from the at least one or first light source for providing the first pair of coherent light beams. The two beam paths of the second pair of beam paths may also part from each other in this first beam splitter which then also splits light coming from the second light source for providing the second pair of coherent light beams. In this case, the light from the first light source and the light from the second light source may differ from each other in wavelength, and the beam paths of the first and of the second pairs of beam paths may include wavelength selective elements.

The two beam paths of the second pair of beam paths may alternatively part from each other in a second beam splitter which splits light coming from the second light source for providing the second pair of coherent light beams. In this case, the second light source may include the at least one or first light source and an optical delay of a greater length than a coherence length or pulse length of the first light source.

With a light source of particularly short coherent length or pulse length it is also possible that the two beam paths of the first and of the second pairs of beam paths part from each other in a common beam splitter which splits light coming from a common light source for providing the first and the second pairs of coherent light beams, if the first and the second pairs of beam paths differ from each other in optical length by more than the coherence length or pulse length of the common light source. These differences in optical length may for example be provided by different optical delays arranged in the different partial areas of the pupils of the objectives.

In case of a difference in optical length by more than the coherence length, the light beams of the different pairs will not interfere with each other even if they reach the common focal area at a same point in time. In case of a difference in optical length by more than the pulse length, the light beams of the different pairs will not interfere with each other even if they are still coherent as they do not reach the common focal area at a same point in time. This way of interference avoidance by means of a non overlapping timing sequence of the light beams of the different pairs is particularly suitable when slow processes are to be influenced by the light intensity distribution formed with the apparatus disclosed here, like for example in RESOLFT fluorescence light microscopy.

Further, it is possible that the two beam paths of the first and of the second pair of beam paths part from each other in a common beam splitter which splits light coming from a common light source for providing the first and the second pairs of coherent beams, wherein the first and the second pairs of coherent beams differ from each other in polarization. It is, however, only possible to have two pairs of coherent light beams with such a difference in polarization that their light intensities in the focal area do not interfere with each other. The ways of avoiding an interference between the pairs of coherent light beams by means of optical delays or different wavelengths are also applicable for more than two pairs of coherent light beams.

In the apparatus for forming a three-dimensional light intensity distribution disclosed here it is not essential that the two objectives facing each other exactly have a common focal point or that the two beam paths of each pair of beam paths differ from each other by $\lambda(2n+1)/2$ exactly at such a common focal point or at the center of the common focal area. The planes at which this criterion is fulfilled may even be shifted in different directions along the common optical axis for the different pairs of beam paths. As two tilted planes will always intersect in a line, and three tilted planes will always intersect in a point, the apparatus will nevertheless form the desired light intensity distribution comprising a spatially limited area of minimum light intensity that is enclosed by areas of higher light intensity. This means that the apparatus is not sensitive to any adjustment errors.

The present invention also relates to a scanning fluorescence light microscope comprising the apparatus according to the invention for forming a three-dimensional light intensity distribution of light which displays a spatially limited area of minimum light intensity that is enclosed by areas of high light intensity. Such a microscope of the present invention further comprises a detector detecting fluorescence light stemming from the common focal area and passed through at least one of the two objectives, and a scanner for shifting the common focal area with regard to a sample stage configured for holding a sample in which a structure of interest is marked with a fluorescent marker.

The light of the three-dimensional light distribution which displays a spatially limited area of minimum light intensity that is enclosed by areas of high light intensity might be fluorescence excitation light, like it is required in a variant of a 4Pi GSD scanning fluorescence light microscope. In such a microscope, the fluorescent marker is intensely excited in the areas of high light intensity but not in the close or spatially limited area of minimum light intensity resulting in an inverse image of the fluorescent marker.

In another embodiment, the scanning fluorescence light microscope of the present invention is a 4Pi STED, RESOLFT or another variant of a 4Pi GSD scanning fluorescence light microscope. Such a microscope uses the apparatus according to the invention for forming a three-dimensional light distribution with a spatially limited area of minimum light intensity that is enclosed by areas of high light intensity of fluorescence inhibiting light. The microscope further comprises a fluorescence excitation device providing fluorescence excitation light which is focused by at least one of the two objectives such that an intensity of the fluorescence excitation light is maximum at a focal point in the common focal area.

Referring now in greater detail to the drawings, FIG. 1 illustrates an apparatus 1 comprising two objectives 2 and 3 which are facing each other on a common optical axis 4 and which focus light coming out of opposite directions into a common focal area around a common focal point 5. Both objectives 2 and 3 have a pupil 40 and 50, respectively. In these pupils, optical delays 6 and 7 are arranged on opposite sides of the optical axis 4 such that the light passing through the objective 2 on the left hand side of the optical axis 4 and the light passing through the objective 3 on the right hand side of the optical axis 4 in FIG. 1 is delayed. The optical delays 6 and 7 delay the light passing through them by such a long time that it does no longer interfere with the light not passing through the delays 6 and 7 in the focal area around the focal point 5 despite all light coming from a common coherent light source 8 having a certain coherence length. I.e. the optical delays 6 and 7 provide an additional optical path which is longer than the coherence length or pulse length of the light source 8. The optical delays 6 and 7 divide the pupils 40 and 50 into different pupil partial areas. The result of this division is that, in the focal area around the focal point 5, only the two coherent beams 9 and 10 of a first pair of coherent light beams which pass through the delays 6 and 7, on the one hand, and the two coherent beams 11 and 12 of a second pair of coherent light beams which do not pass through the delays 6 and 7 interfere with each other, whereas there is no interference between these two pairs of coherent beams 9 and 10, and 11 and 12, respectively.

With a difference in optical length of the beam paths 13 and 14 of the beams 9 and 10 and of the beam paths 15 and 16 of the beam paths 11 and 12 of $\lambda(2n+1)/2$ each, wherein is the wavelength of the light of the light beams, the result of the interference of the coherent beams 9 and 10 is a spatially limited area of zero or minimum light intensity which extends along a plane 17 tilted with regard to a common focal plane 18 of the two objectives 2 and 3. The tilt of the plane 17 is due to the fact that the beams 9 and 10 are offset from the optical axis 4 in opposite directions. Similarly, a spatially limited area of minimum light intensity resulting from the interference of the beams 11 and 12 which includes the focus point 5 extends along a plane 19 which is also tilted with regard to the common focal plane 18 but in an opposite direction. The total light intensity in the focal area around the focal point 5 comprises the light intensities of both interference patterns of the pair of beams 9 and 10 and of the pair of beams 11 and 12, i.e. their areas of higher light intensity on both sides of the planes 17 and 19. The remaining area of minimum light intensity extends along an axis running perpendicular to the drawing plane through the focal point 5. In other words, splitting the pupils 40 and 50 of the objectives 2 and 3 in different pupil partial areas and only allowing interference of light passing through pairs of these pupil partial areas centered on opposite sides of the optical axis 4 reduces the extension of a spatially limited area of minimum light intensity around the focal point 5. Without this division of the pupils the spatially limited area of minimum light intensity would extend along the common focal plane 18.

The apparatus 1 further comprises a beam splitter 20 at which the beam paths 13 and 14, and 15 and 16, respectively, part from each other on their way from the light source 8 to the objectives 2 and 3. The apparatus 1 further comprises mirrors 29 and 30 at which the beam paths 13 and 15, and 14 and 16, respectively, are reflected on their way from the light source 8 to the objects 2 and 3. The apparatus 1 may be part of a scanning fluorescence light microscope 21 which further comprises the following parts indicated in FIG. 1 with dashed lines only:

a light source 22 providing excitation light 23 which is coupled into the beam path towards the objective 1 by means of a dichroic mirror 24;

a detector 25 detecting fluorescence light 26 stemming from the focal area including the focal point 5 which passed through the objective 3 and is deflected towards the detector 25 by means of a further dichroic mirror 27; and a scanner shifting the focal point 5 relative to a sample stage, which is only indicated by means of a double-headed arrow 28 here.

Figure 2:
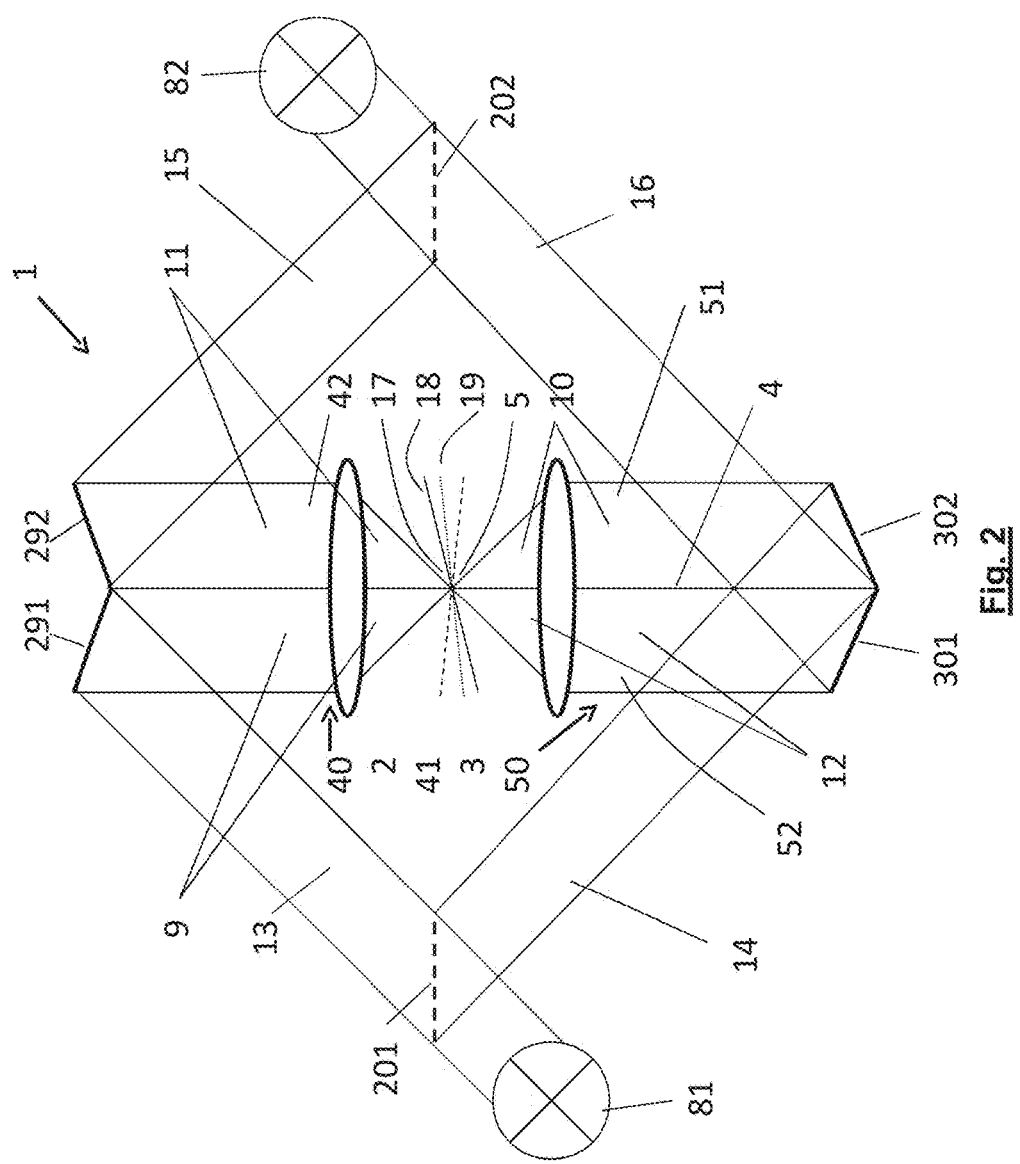
FIG. 2 is a schematic drawing showing a second embodiment of the apparatus according to the present invention.

The embodiment of the apparatus 1 depicted in FIG. 2 comprises no optical delays 6 and 7 according to FIG. 1. Instead, the coherent light beams 9 and 10, and 11 and 12, respectively, of the two pairs of light beams come from separate coherent light sources 81 and 82 that are mutually incoherent where. The two light beams from each light source are separately coherently added in the focal area by means of pairs of mirrors 291 and 292, and 301 and 302, respectively. The beam paths 13 and 14, and 15 and 16, respectively, which extend from these two light sources 81 and 82 may partially overlap in the pupils 40 and 50 without interfering with each, or they may even completely overlap along a part of their length terminating at the pupils 40 and 50 where they are separated by wavelength selective elements, if the light sources 81 and 82 differ in wavelength, for example.

Figure 3:
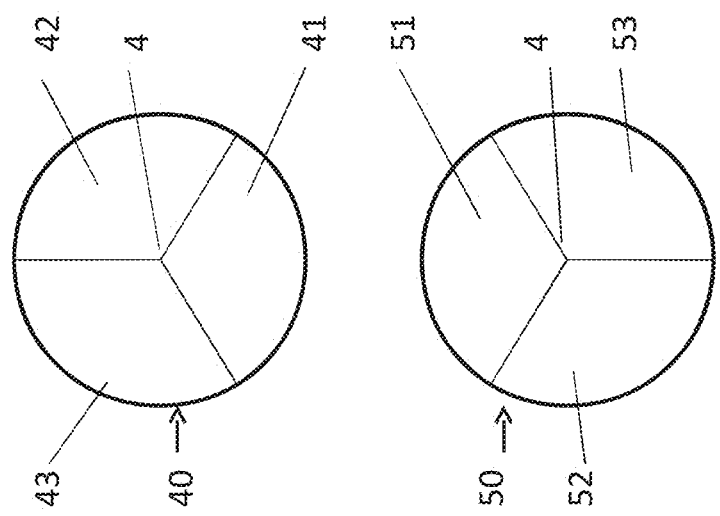
FIG. 3 shows pupils of two objectives of a further embodiment of the apparatus according to the present invention both divided up into three pupil partial areas, the pupil partial areas of both pupils forming pairs.

FIG. 3 illustrates the division of the pupils 40 and 50 of a further embodiment of the apparatus 1, both pupils 40 and 50 being viewed in a same direction along the optical axis 4. The pupil 40 is divided in three pupil partial areas 41, 42 and 43 which are rotational symmetric to each other with respect to the optical axis 4. The pupil 50 is divided in pupil partial areas 51, 52 and 53 which are also rotational symmetric to each other with respect to the optical axis 4. The light passing through the pupils 40 and 50 forms three pairs of coherent light beams interfering in the focal area around the common focal point of the two objectives to which the pupils 40 and 50 belong. The coherent light beams of one pair do, however, not interfere with the coherent beams of any other pair. As a result, there are three partial light intensity distributions each having a spatially limited area of minimum light intensity extending along a plane tilted in another direction with regard to the common focal plane of the two objectives. Particularly, the coherent light beams passing through the pupil partial areas 41 and 51 interfere with each other as do the coherent light beams passing through the pupil partial areas 42 and 52 as do the coherent light beams passing through the pupil partial areas 43 and 53. The number of pupil partial areas 41 to 43 and 51 to 53 may also be increased to four or more, but this will merely make the apparatus more complicated but provides little additional effect with regard to spatially limiting the area of minimum light intensity of the overall light intensity distribution around the common focal point of the objectives.

Figure 4:
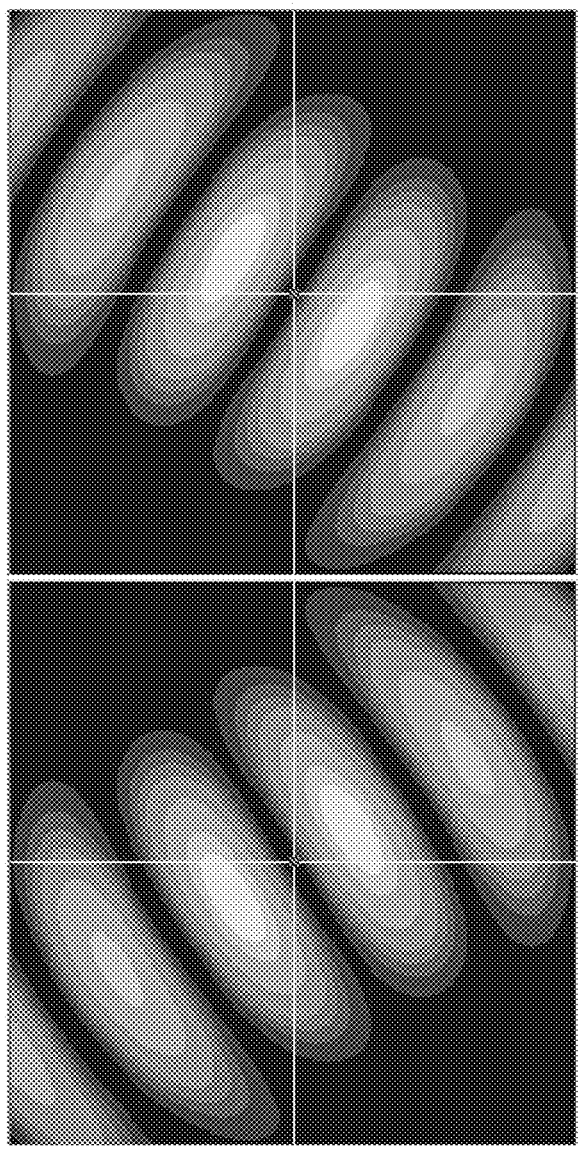
FIG. 4 separately illustrates the light intensity distributions resulting from the interference between coherent light beams of two pairs of coherent light beams offset from the optical axis in opposite directions.

FIG. 4 separately illustrates the light intensity distributions or interference patterns of two pairs of coherent light beams in the focal area around the common focal point of the objectives of the apparatus according to the present invention. These interference patterns provide spatially limited areas of minimum light intensity extending along a plane tilted with regard to the common focal plane of the objectives in different directions as already explained when describing FIG. 1. FIG. 4 and the following figure indicate the light intensities in a gray scale in which a brighter area represents an area of a higher light intensity.

FIG. 5 shows sections through the spatially limited area of minimum light intensity of the overall light intensity distribution resulting from one pair of coherent light beams (a), two pairs of coherent light beams (b) and three pairs of coherent light beams (c). (a) represents the prior art of 4Pi fluorescence light microscopy in which the light intensity distribution of fluorescence inhibiting light has a minimum extending along the common focal plane of the objectives and thus only provides an enhanced spatial resolution in z-direction. (b) is the case of FIGS. 1 and 2 in which two pairs of coherent light beams which do not interfere are combined and reduce the spatially limited area of minimum light intensity of the overall light intensity distribution to an area around an axis extending through the common focal point of the objectives. (c) shows an area of minimum light intensities spatially limited in all directions and of a very small volume, i.e. a nearly point-shaped zero point of the overall three-dimensional light intensity distribution. The gradient of the light intensity distribution between the area of minimum light intensity and the areas of high light intensity is even stronger than in case of isoSTED fluorescence light microscopy as could be shown in calculations of the intensity distribution around the common focal point of the objectives considering the same light intensities.

Generally, the light intensity in the area of higher light intensity is essentially higher than the light intensity in the area of minimum light intensity, which is preferably zero or close to zero. Preferably, the maximum light intensity in the area of higher light intensity is at least five times, more preferably it is at least ten times or one hundred times or even multiple hundred times higher than the light intensity in the area of minimum light intensity. This is in accordance with an understanding that the area of high light intensity is the area in which the light intensity of fluorescence inhibiting light exceeds a saturation light intensity which is required to essentially completely inhibit the emission of fluorescence of the fluorescent marker in spite of being illuminated with excitation light and which depends on the fluorescent marker. (Vice versa, in case of excitation light, the area of high light intensity is the area in which the light intensity of the excitation light exceeds a saturation light intensity which provides for a saturated excitation of the fluorescent marker for fluorescence and which also depends on the fluorescent marker.) In the same manner, the area of minimum light intensity is understood as the area in which the light intensity of the fluorescence inhibiting light is lower than the saturation light intensity, and thus the emission of fluorescence of the fluorescent marker is not effectively inhibited in the area of minimum light intensity.

Figure 6:
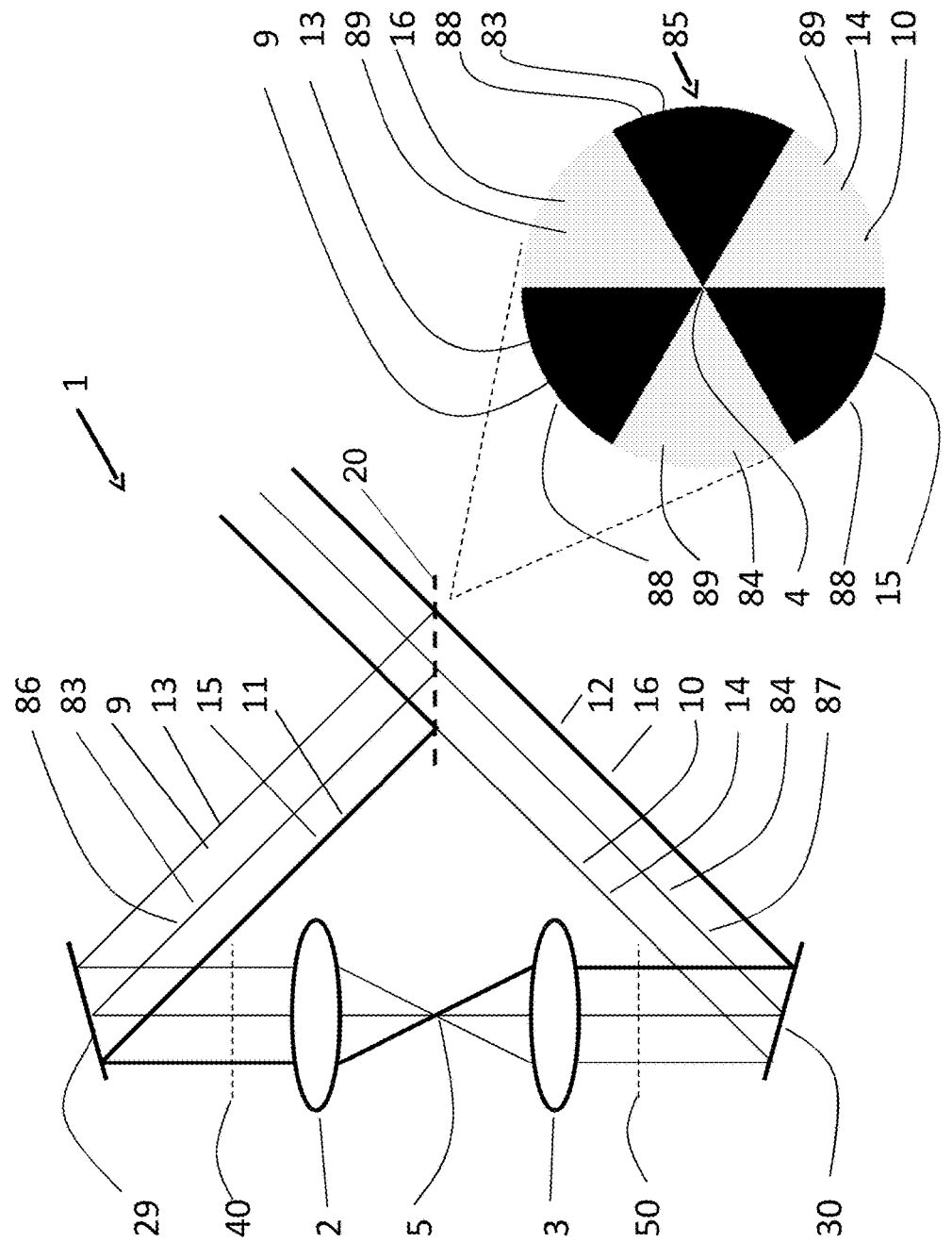
FIG. 6 is a schematic drawing showing a major components of a further embodiment of the apparatus according to the present invention.

FIG. 6 shows the relevant components of a further embodiment of the apparatus 1 in which three pairs of beam paths 13 and 14, 15 and 16, and 83 and 84, respectively, are defined. These beam paths pass through the pupils 40 and 50 of the objectives 2 and 3 in the pupils partial areas 41 and 51, 42 and 52, and 43 and 53, respectively, as shown in FIG. 3. The pairs of coherent light beams 9 and 10, 11 and 12, and 86 and 87, respectively, which are running along these beams paths, come from three different coherent light sources not depicted here. Each pair of coherent light beams 9 and 10, 11 and 12, and 86 and 87, respectively, is separated at the beam splitter 20 which is segmented mirror here, whose reflecting segments 88 and transmitting segments 89 are additionally shown in an enlarged front view of the segmented mirror 85 in FIG. 6. Each segment 88 reflects one light beam 13, 15 or 86 of each of the pairs of coherent light beams, whereas a transmitting segment 89 located on the opposite side of the optical axis 4 transmits the respective other light beam 14, 16 or 87. Mirrors 29 and 30 reflect the light beams 13, 15 and 86, and 14, 16 and 87, respectively, towards the objects 2 and 3, respectively.

Many variations and modifications may be made to the preferred embodiments of the invention without departing substantially from the spirit and principles of the invention. All such modifications and variations are intended to be included herein within the scope of the present invention, as defined by the following claims.

I claim:

1. An apparatus for forming a three-dimensional light intensity distribution comprising a spatially limited area of minimum light intensity that is enclosed by areas of higher light intensity, the apparatus comprising:
   two objectives
      which are facing each other on a common optical axis,
      which focus light coming out of opposite directions into a common focal area, and
      which each have a pupil, the common optical axis passing through a center of the pupil,
   at least one light source, and
   a first pair of beam paths each extending from the at least one light source, through one of the objectives and to the common focal area, wherein light intensities of a first pair of coherent light beams each coming from the at least one light source and running along one of the beam paths of the first pair of beam paths extinguish each other in a first partial area of the focal area by destructive interference as the two beam paths of the first pair of beam paths differ from each other in optical length by $\lambda 1\ (2n+1)/2$, wherein $\lambda 1$ is the wavelength of the light of the first pair of coherent light beams and n is an integer,
   wherein each of the beam paths of the first pair of beam paths pass passes through one of the two objectives in a first pair of partial areas of the pupils of the objectives centered on opposite sides of the common optical axis,
   wherein the apparatus further comprises a second pair of beam paths each extending from the at least one or a second light source, through one of the objectives and to the common focal area, wherein light intensities of a second pair of coherent light beams each coming from the at least one or the second light source and running along one of the beam paths of the second pair of beam paths extinguish each other in a second partial area of the focal area by destructive interference as the two beam paths of the second pair of beam paths differ from each other in optical length by $\lambda 2\ (2m+1)/2$, wherein $\lambda 2$ is the wavelength of the light of the second pair of coherent light beams and m is an integer,
   wherein each of the beam paths of the second pair of beam paths passes through one of the two objectives in one of a second pair of partial areas of the pupils of the objectives centered on opposite sides of the common optical axis,
   wherein the two partial areas of the second pair of partial areas of the pupils of the objectives are offset in a rotational direction about the common optical axis with regard to the two partial areas of the first pair of partial areas of the pupils of the objectives, and
   wherein the light of the second pair of coherent light beams does not interfere with the light of the first pair of coherent light beams in the common focal area as the light of the second pair of coherent light beams and the light of the first pair of coherent light beams display at least one of the following features: they are non-coherent, their wavelengths are not identical, their polarizations are not identical, and they do not coincide in time.

2. The apparatus of claim 1, further comprising at least one further pair of beam paths each extending from the at least one or a further light source, through one of the objectives and to the common focal area, wherein light intensities of a further pair of coherent light beams each coming from the at least one or the further light source and running along one of the beam paths of the at least one further pair of beam paths extinguish each other in a further partial area of the focal area by destructive interference as the two beam paths of the at least one further pair of beam paths differ from each other in optical length by $\lambda 3\ (2p+1)/2$, where $\lambda 3$ is the wavelength of the light of the further pair of coherent light beams and p is an integer,
   wherein each of the beam paths of the at least one further pair of beam paths passes through one of the two objectives in one of a first pair of partial areas of the pupils of the objectives centered on opposite sides of the common optical axis,
   wherein the two partial areas of the further pair of partial areas of the pupils of the objectives are offset in the rotational direction about the common optical axis with regard to the two partial areas of all other pairs of partial areas of the pupils of the objectives, and
   wherein the light of the further pair of coherent light beams does not interfere with the light of any other pair of coherent light beams in the common focal area as the light of the further pair of coherent light beams and the light of any other pair of coherent light beams display at least one of the following features: they are non-coherent, their wavelengths are not identical, their polarizations are not identical, and they do not coincide in time.

3. The apparatus of claim 1, wherein no partial area of the pupils of the objectives extends beyond the common optical axis, and/or wherein the partial areas of the pupil of each of the objectives through which the different beam paths pass towards the common focal area do not overlap.

4. The apparatus of claim 1, wherein the two partial areas of each pair of partial areas of the pupils of the objectives are point symmetric with regard to the common focal area.

5. The apparatus of claim 1, wherein the partial areas of the pupil of each of the objectives through which the different beam paths pass towards the common focal area are rotationally symmetric with regard to the common optical axis.

6. The apparatus of claim 1, wherein the two beam paths of the first pair of beam paths part from each other in a first beam splitter which splits light coming from the at least one light source for providing the first pair of coherent light beams.

7. The apparatus of claim 6, wherein the two beam paths of the second pair of beam paths part from each other in the first beam splitter which also splits light coming from the second light source for providing the second pair of coherent light beams.

8. The apparatus of claim 7, wherein the light from the at least one light source and the light from the second light source differ from each other in wavelength, and wherein the beam paths of the first and of the second pairs of beam paths include wavelength selective elements.

9. The apparatus of claim 6, wherein the two beam paths of the second pair of beam paths part from each other in a second beam splitter which splits light coming from the second light source for providing the second pair of coherent light beams.

10. The apparatus of claim 6, wherein the two beam paths of the second pair of beam paths part from each other in a second beam splitter which splits light coming from the first light source for providing the second pair of coherent light beams, and wherein an optical delay of a greater length than a coherence length or pulse length of the at least one light source is arranged between the at least one light source and the second beam splitter.

11. The apparatus of claim 1, wherein the two beam paths of the first and of the second pairs of beam paths part from each other in a common beam splitter which splits light coming from the at least one light source for providing the first and the second pairs of coherent light beams, and wherein the first and the second pairs of beam paths differ from each other in optical length by more than a coherence length or pulse length of the at least one light source.

12. The apparatus of claim 1, wherein the two beam paths of the first and of the second pairs of beam paths part from each other in a common beam splitter which splits light coming from the at least one light source for providing the first and the second pairs of coherent light beams, and wherein the first and the second pairs of coherent light beams differ from each other in polarization.

13. A scanning fluorescence light microscope comprising
an apparatus for forming a three-dimensional light intensity distribution comprising a spatially limited area of minimum light intensity that is enclosed by areas of higher light intensity, the apparatus comprising:
two objectives
which are facing each other on a common optical axis,
which focus light coming out of opposite directions into a common focal area, and
which each have a pupil, the common optical axis passing through a center of the pupil,
at least one light source, and
a first pair of beam paths each extending from the at least one light source, through one of the objectives and to the common focal area, wherein light intensities of a first pair of coherent light beams each coming from the at least one light source and running along one of the beam paths of the first pair of beam paths extinguish each other in a first partial area of the focal area by destructive interference as the two beam paths of the first pair of beam paths differ from each other in optical length by $\lambda 1 (2n+1)/2$, wherein $\lambda 1$ is the wavelength of the light of the first pair of coherent light beams and n is an integer,
wherein each of the beam paths of the first pair of beam paths pass through one of the two objectives in one of a first pair of partial areas of the pupils of the objectives centered on opposite sides of the common optical axis,
wherein the apparatus further comprises a second pair of beam paths each extending from the at least one or a second light source, through one of the objectives and to the common focal area, wherein light intensities of a second pair of coherent light beams each coming from the at least one or the second light source and running along one of the beam paths of the second pair of beam paths extinguish each other in a second partial area of the focal area by destructive interference as the two beam paths of the second pair of beam paths differ from each other in optical length by $\lambda 2 (2m+1)/2$, wherein $\lambda 2$ is the wavelength of the light of the second pair of coherent light beams and m is an integer,
wherein each of the beam paths of the second pair of beam paths pass through one of the two objectives in one of a second pair of partial areas of the pupils of the objectives centered on opposite sides of the common optical axis,
wherein the two partial areas of the second pair of partial areas of the pupils of the objectives are offset in a rotational direction about the common optical axis with regard to the two partial areas of the first pair of partial areas of the pupils of the objectives, and
wherein the light of the second pair of coherent light beams does not interfere with the light of the first pair of coherent light beams in the common focal area as the light of the second pair of coherent light beams and the light of the first pair of coherent light beams display at least one of the following features: they are non-coherent, their wavelengths are not identical, their polarizations are not identical, and they do not coincide in time;
a detector detecting fluorescence light stemming from the common focal area and passed through at least one of the two objectives; and
a scanner for shifting the common focal area with regard to a sample stage.

14. The scanning fluorescence light microscope of claim 13, further comprising
a fluorescence excitation device providing fluorescence excitation light which is focused by at least one of the two objectives to a focal point in the common focal area,
wherein the light of the second pair of coherent light beams and the light of the first pair of coherent light beams provided by the apparatus is fluorescence inhibiting light.

* * * * *